(12) United States Patent
Chung et al.

(10) Patent No.: US 11,072,636 B2
(45) Date of Patent: Jul. 27, 2021

(54) PEPTIDE FOR INHIBITING ANGIOGENESIS AND USE THEREOF

(71) Applicant: CAREGEN CO., LTD., Anyang-si (KR)

(72) Inventors: Yong Ji Chung, Seoul (KR); Eun Mi Kim, Yongin-si (KR); Eung Ji Lee, Anyang-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 16/649,327

(22) PCT Filed: Mar. 14, 2018

(86) PCT No.: PCT/KR2018/002978
§ 371 (c)(1),
(2) Date: Mar. 20, 2020

(87) PCT Pub. No.: WO2019/059476
PCT Pub. Date: Mar. 28, 2018

(65) Prior Publication Data
US 2020/0277332 A1  Sep. 3, 2020

(30) Foreign Application Priority Data
Sep. 22, 2017 (KR) .................. 10-2017-0122571

(51) Int. Cl.
| | |
|---|---|
| *A61K 38/08* | (2019.01) |
| *A61K 38/10* | (2006.01) |
| *A61K 38/00* | (2006.01) |
| *C07K 7/06* | (2006.01) |
| *C07K 7/08* | (2006.01) |
| *C07K 7/00* | (2006.01) |
| *A23L 33/18* | (2016.01) |

(52) U.S. Cl.
CPC ............... *C07K 7/06* (2013.01); *A23L 33/18* (2016.08); *A23V 2002/00* (2013.01); *A61K 38/00* (2013.01)

(58) Field of Classification Search
CPC ........ A61K 38/00; A61K 38/08; A61K 38/10; C07K 7/00; C07K 7/06; C07K 7/08
USPC .......... 514/13.3, 21.6, 21.5, 21.4, 21.3, 1.1; 530/300, 328, 327, 326, 325, 324
See application file for complete search history.

(56) References Cited

U.S. PATENT DOCUMENTS

| | | | |
|---|---|---|---|
| 6,319,687 B1 | 11/2001 | Chader et al. |
| 8,778,329 B2 | 7/2014 | Seavey et al. |
| 9,610,318 B2 | 4/2017 | Cho et al. |
| 9,938,320 B2 | 4/2018 | Cho et al. |
| 10,034,922 B2 | 7/2018 | Kim |
| 2005/0250694 A1 | 11/2005 | Ma |
| 2006/0189519 A1 | 8/2006 | Volz et al. |
| 2009/0069241 A1 | 3/2009 | Barnstable et al. |
| 2009/0118191 A1 | 5/2009 | Volz et al. |
| 2012/0316115 A1 | 12/2012 | Volpert et al. |
| 2013/0137637 A1 | 5/2013 | Cho et al. |
| 2016/0296604 A1 | 10/2016 | Kim |
| 2017/0166609 A1 | 6/2017 | Cho et al. |

FOREIGN PATENT DOCUMENTS

| | | |
|---|---|---|
| KR | 10-2011-0046911 A | 5/2011 |
| KR | 10-1335203 B | 11/2013 |
| KR | 10-2016-0079881 A | 7/2016 |
| WO | 2004/028559 A1 | 4/2004 |
| WO | 2013/184986 A2 | 12/2013 |

OTHER PUBLICATIONS

Auerbach et al., "Angiogenesis assays: Problems and pitfalls," Cancer and Metastasis Reviews, 2000, 19: 167-172. (Year: 2000).*
Jain RK, "Barriers to Drug Delivery in Solid Tumors," Scientific American, 1994, 58-65. (Year: 1994).*
Albini et al., "Cancer prevention by targeting angiogenesis," Nature, 2012, 1-12. (Year: 2012).*
Folkman, "Angiogenesis in cancer, vascular, rheumatoid and other disease", Nal Med., 1(1): 27-31 (1995).
Zhang et al., "Pigment epithelium-derived factor downregulates vascular endothelial growth factor (VEGF) expression and inhibits VEGF-VEGF receptor 2 binding in diabetic retinopathy", Journal of Molecular Endocrinology, 37, 1-12 (2006).
Risau, "Mechanisms of angiogenesis", Nature, 386 (6626): 671-674 (1997).
Dong-Woon, "Effect of Novel Synthetic Peptide on angiogenesis", Seoul National University School of Dentistry (2014).
International Search Report and Written Opinion from International Application No. PCT/KR2018/002978, dated Jun. 11, 2018.
International Preliminary Report on Patentability from International Application No. PCT/KR2018/002978, dated Mar. 24, 2020.
First Examination Report for Australian Application No. 2018335193, dated Jun. 10, 2020.
Rajabi, M. et al., "The Role of Angiogenesis in Cancer Treatment", Biomedicines, 5(34): 1-12 (2017).
Yadav, L. et al., "Tumour Angiogenesis and Angiogenic Inhibitors: A Review", Journal of Clinical and Diagnostic Research, 9(6): 1-5 (Jun. 2015).
Zirlik, K. et al., "Anti-Angiogenics: Current Situation and Future Perspectives", Oncology Research and Treatment, 41: 166-171 (2018).
Extended European Search Report for European Patent Application No. 18858492.4 dated Oct. 20, 2020, 47 pages.

* cited by examiner

*Primary Examiner* — Julie Ha
(74) *Attorney, Agent, or Firm* — Merchant & Gould P.C.

(57) ABSTRACT

Peptide having an angiogenesis inhibitory activity and a use of the peptide, related to the treatment or prevention of excessive angiogenesis-related diseases. Particularly, a novel peptide that binds, in competition with vascular endothelial growth factors (VEGF), to VEGF receptors and can significantly inhibit the proliferation, migration and differentiation of vascular endothelial cells, thereby being effectively usable as an active ingredient of a composition or a health functional food for preventing or treating diseases, such as macular degeneration, a tumor, arthritis or psoriasis, caused by excessive angiogenesis.

7 Claims, 8 Drawing Sheets

Specification includes a Sequence Listing.

PEPTIDE FOR INHIBITING ANGIOGENESIS AND USE THEREOF

This application is a National Stage Application of International Application No. PCT/KR2018/002978, filed Mar. 14, 2018, which claims benefit of Serial No. 10-2017-0122571, filed Sep. 22, 2017 in the Republic of Korea and which applications are incorporated herein by reference. To the extent appropriate, a claim of priority is made to each of the above disclosed applications.

TECHNICAL FIELD

The present invention relates to a novel peptide having an angiogenesis inhibitory activity and use of the peptide associated with the treatment or prevention of excessive angiogenesis-related diseases.

BACKGROUND ART

Angiogenesis is a biological process that provides new blood vessels to tissues or organs, and specifically, refers to the generation of new capillaries from existing microvascular vessels, and is a fundamental process of generating blood vessels in the body after growth. Physiological angiogenesis normally observed in the human body occurs only in very limited situations, such as development of embryo and fetus, maturation of uterus, proliferation of placenta, formation of corpus lutea, and wound healing, and even at this time, if the physiological angiogenesis is also very tightly regulated so that necessary functions are achieved, the angiogenesis stops. The generation of new blood vessels is tightly regulated by an angiogenesis regulating factor, and phenotypes of angiogenesis have been reported to be changed due to an overall balance between up-regulation of angiogenesis stimulating factors and down-regulation of angiogenesis inhibiting factors (Folkman J., *Nat. Med.*, 1(1): 27-31 (1995)).

The process of generating newly blood vessels is very complex and sophisticated, but in summary, the process is as follows. First, when stimuli for angiogenesis are delivered to existing blood vessels, the blood vessels are expanded and membrane permeability increases. Second, fibrin is released out of the blood vessel through the expanded blood vessel and then deposited on the cytoplasmic matrix around the blood vessel. Third, enzymes to decompose basement membranes of the existing blood vessels are activated, and the basement membranes are destroyed, and endothelial cells are released from the blood vessels therebetween, and then proliferated and migrated from the matrix of surrounding cells. Finally, endothelial cells arranged in a row form a tube to generate new blood vessels (Risau W., Nature, 386 (6626): 671-674 (1997)).

The diseases associated with angiogenesis appearing in a pathological state may be greatly classified into inflammatory diseases such as arthritis, ophthalmic diseases such as diabetic retinopathy, dermatological diseases such as psoriasis, and cancer as the most representative disease (Folkman J., Nat. Med., 1(1): 27-31 (1995)). The ophthalmic diseases caused by angiogenesis include diseases, such as macular degeneration, diabetic retinopathy in which the capillaries in the retina invade the vitreous body and eventually the patient becomes blind due to complications of diabetes mellitus, retinopathy in premature infants, and neovascular glaucoma, and the like, and millions of people are blinded worldwide each year by these diseases. In addition, arthritis is caused by autoimmune abnormality, but known that chronic inflammation caused in the synovial cavity induces angiogenesis during the course of developing the disease, and the arthritis is a disease caused when new capillaries invade joints to destroy cartilage. In addition, the psoriasis is a chronic proliferative disease that occurs in the skin, and for rapid proliferation, since a lot of blood needs to be supplied, angiogenesis cannot help actively occurring.

Meanwhile, a vascular endothelial growth factor (VEGF) among angiogenesis promoting factors activates various signaling chain reactions and plays a role in inducing the proliferation, migration and differentiation of endothelial cells. Accordingly, biological activity and signaling chain reaction of VEGF may be inhibited by using neutralizing antibodies and signal inhibitors of the VEGF to become a therapeutic strategy capable of treating various diseases associated with angiogenesis.

However, even though angiogenesis inhibiting drugs targeting VEGF or VEGF receptors may treat a variety of diseases associated with abnormal angiogenesis, there is still no known peptide that binds to the VEGF receptors in competition with the VEGF and significantly inhibits the proliferation, migration and differentiation of vascular endothelial cells.

DISCLOSURE

Technical Problem

An object of the present invention is to provide a novel peptide for inhibiting angiogenesis.

Another object of the present invention is to provide use of the novel peptide for the prevention or treatment of angiogenesis-related diseases.

Technical Solution

In order to achieve the objects, an aspect of the present invention provides a peptide for inhibiting angiogenesis comprising an amino acid sequence represented by SEQ ID NO: 1 or 2.

Another aspect of the present invention provides a pharmaceutical composition for the prevention or treatment of angiogenesis-related diseases comprising the peptide as an active ingredient.

Yet another aspect of the present invention provides a health functional food for the prevention or improvement of angiogenesis-related diseases comprising the peptide as an active ingredient.

Advantageous Effects

According to the present invention, the novel peptide binds to vascular endothelial growth factor (VEGF) receptors in competition with VEGFs and significantly inhibits the proliferation, migration and differentiation of vascular endothelial cells, thereby being effectively usable as an active ingredient of a composition for preventing or treating diseases caused by excessive angiogenesis.

However, the effects of the present invention are not limited to the above-mentioned effects, and other effects not mentioned will be clearly understood by those skilled in the art from the following description.

DESCRIPTION OF DRAWINGS

In FIGS. 1 to 14, 'VEGF+SEQ ID NO: 1' represents a group treated with both a VEGF and a peptide having an amino acid sequence of SEQ ID NO: 1, 'VEGF+SEQ ID NO: 2' represents a group treated with both a VEGF and a peptide having an amino acid sequence of SEQ ID NO: 2, and 'VEGF+Sunitinib' or 'VEGF+Suni' represents a group treated with both a VEGF and sunitinib.

BEST MODE

Figure 1:
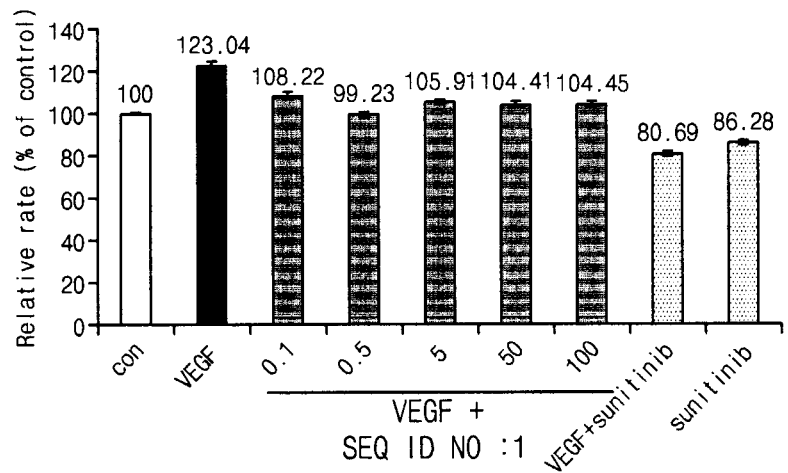
FIGS. 1 and 2 are graphs showing results of confirming an effect of inhibiting the proliferation of vascular endothelial cells by a peptide having an amino acid sequence of SEQ ID NO: 1 and a peptide having an amino acid sequence of SEQ ID NO: 2, respectively.

Hereinafter, the present invention will be described in detail.

1. Peptides for Inhibiting Angiogenesis

An aspect of the present invention provides a novel peptide having an angiogenesis inhibitory activity.

The peptide refers to a polymer consisting of two or more amino acids linked by peptide bonds, and has a disadvantage in that the peptide is not effectively introduced to a target tissue or cell due to a too large size of the peptide itself, and the peptide disappears in the body in a short time due to a short half-life. The peptide of the present invention consists of 20 or less, preferably 15 or less, more preferably 10 or less amino acids having an angiogenesis inhibitory activity.

The novel peptide of the present invention may include an amino acid sequence of SEQ ID NO: 1 or SEQ ID NO: 2 and may be variants or fragments of amino acids having different sequences by deletion, insertion, substitution or combination of amino acid residues within a range that does not affect the angiogenesis inhibitory activity of the peptide. Amino acid exchange at a peptide level that does not change the angiogenesis inhibitory activity of the peptide as a whole has been known in the art. In some cases, the amino acid exchange may be modified by phosphorylation, sulfation, acrylation, glycosylation, methylation, farnesylation, and the like.

Accordingly, the present invention includes a peptide having an amino acid sequence substantially identical to the peptide having the amino acid sequence of SEQ ID NO: 1 or SEQ ID NO: 2, and variants or active fragments thereof. The substantially identical protein refers to an amino acid sequence having sequence homology of 75% or more, preferably 80% or more, more preferably 90% or more, and most preferably 95% or more with the amino acid sequence of SEQ ID NO: 1 or SEQ ID NO: 2. In addition, the peptide may further include an amino acid sequence prepared for a specific purpose to increase a targeting sequence, a tag, labeled residues, a half-life or peptide stability.

The peptide of the present invention may be obtained by various methods well-known in the art. As an example, the peptide may be prepared by using polynucleotide recombination and a protein expression system or prepared by in-vitro synthesis through chemical synthesis such as peptide synthesis, cell-free protein synthesis, and the like.

In addition, in order to obtain better chemical stability, enhanced pharmacological properties (half-life, absorbency, titer, efficacy, etc.), modified specificity (e.g., a wide biological activity spectrum), and reduced antigenicity, a protective group may bind to an N- or C-terminus of the peptide. Preferably, the protective group may be an acetyl group, a fluorenylmethoxy carbonyl group, a formyl group, a palmitoyl group, a myristyl group, a stearyl group, or polyethylene glycol (PEG), but may include any ingredient that may enhance the modification of the peptide, particularly the stability of the peptide, without limitation.

The 'stability of the peptide' means not only in-vivo stability that protects the peptides of the present invention from the attack of protein cleavage enzymes in vivo, but also storage stability (e.g., room-temperature storage stability).

In order to confirm an effect of inhibiting the proliferation and differentiation of vascular endothelial cells by the peptides of the present invention, in a specific exemplary embodiment of the present invention, the vascular endothelial cells are treated with a peptide having an amino acid sequence of SEQ ID NO: 1 or SEQ ID NO: 2 and then the degree of proliferation and differentiation of vascular endothelial cells was confirmed. As a result, it was confirmed that the proliferation and differentiation of vascular endothelial cells induced by the VEGF was reduced depending on whether the peptide of the present invention was treated (see FIGS. 1 to 4).

Figure 5:
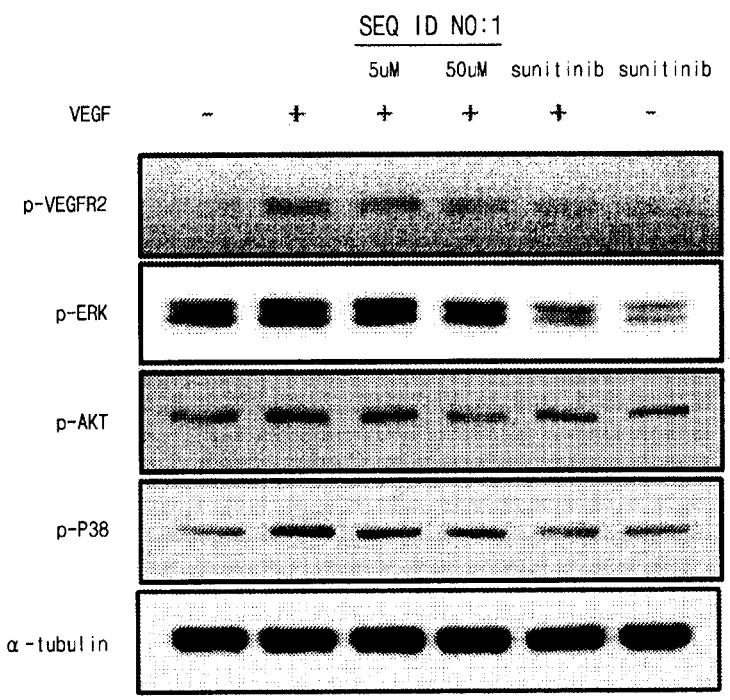
FIGS. 5 and 6 are diagrams showing results of confirming an effect of inhibiting a cell signaling pathway induced by a VEGF by a peptide having an amino acid sequence of SEQ ID NO: 1 and a peptide having an amino acid sequence of SEQ ID NO: 2, respectively.
Figure 6:
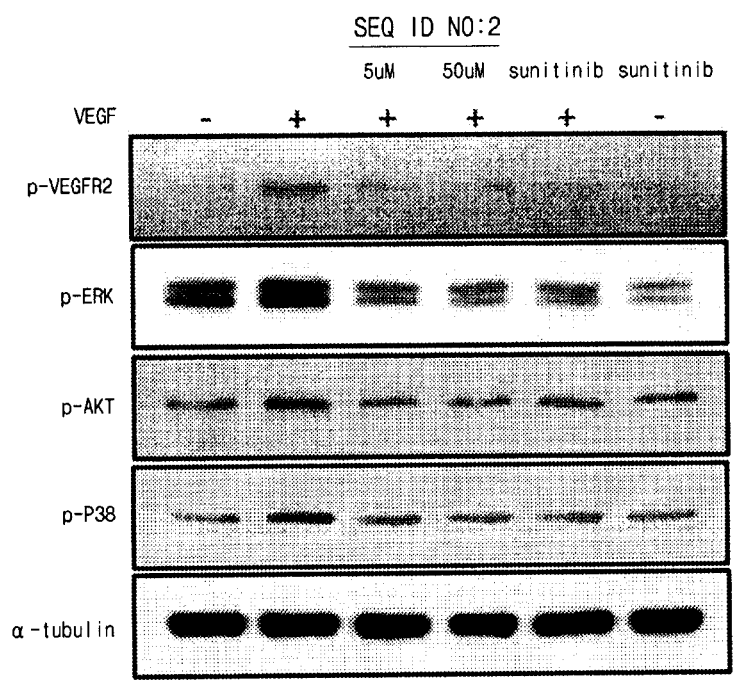

Further, in order to confirm the effect of inhibiting a cell signaling pathway induced by the VEGFs by the peptides of the present invention, in a specific exemplary embodiment of the present invention, a peptide having an amino acid sequence of SEQ ID NO: 1 or SEQ ID NO: 2 was treated to vascular endothelial cells and then changes in phosphorylation of a VEGF receptor (VEGFR2), ERK, AKT and p38 induced by the VEGF were confirmed. As a result, it was confirmed that the peptides of the present invention significantly inhibited the phosphorylation of VEGFR2, ERK, AKT and p38 induced by the VEGF (see FIGS. 5 and 6).

Figure 7:
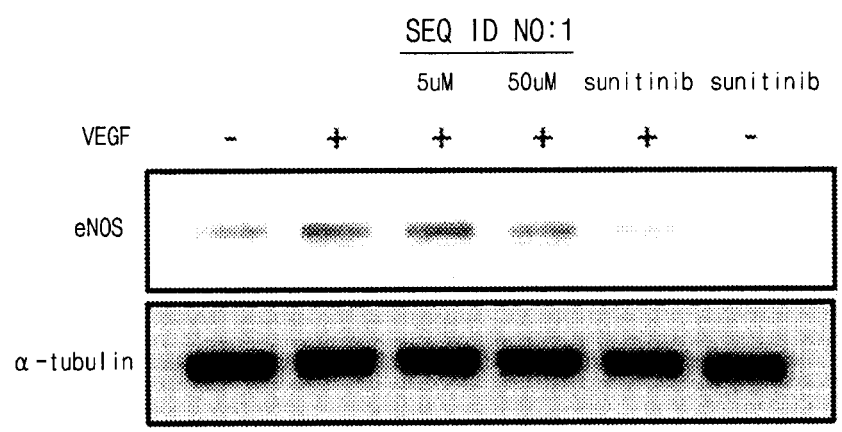
FIGS. 7 and 8 are diagrams showing results of confirming an effect of changing an expression level of an eNOS protein by a peptide having an amino acid sequence of SEQ ID NO: 1 and a peptide having an amino acid sequence of SEQ ID NO: 2, respectively.
Figure 8:
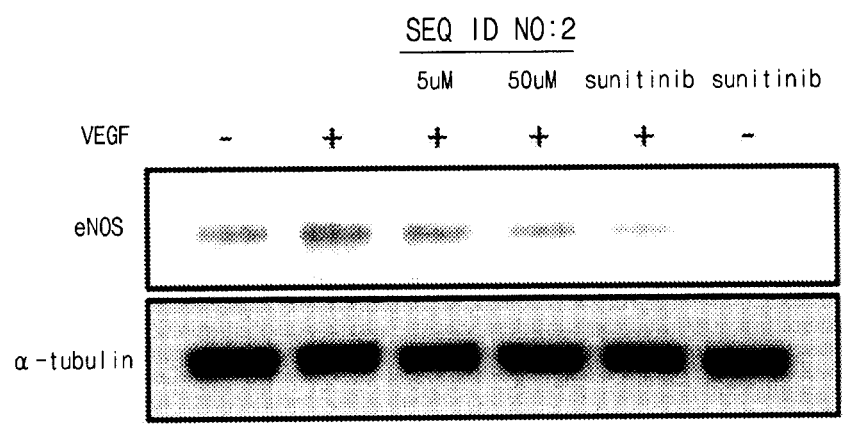

In addition, in order to confirm an effect of inhibiting the migration the vascular endothelial cells by the peptides of the present invention, in a specific exemplary embodiment of the present invention, a change in expression level of a vascular endothelial cell migration marker 'eNOS' was confirmed depending on treatment of the peptide having the amino acid sequence of SEQ ID NO: 1 or SEQ ID NO: 2 to the vascular endothelial cells. As a result, the peptides of the present invention were confirmed to decrease concentration-dependently the eNOS expression increased by VEGF treatment (see FIGS. 7 and 8).

Figure 9:
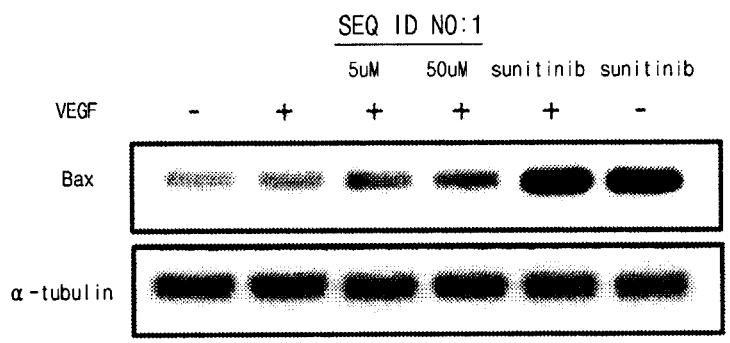
FIGS. 9 and 10 are diagrams showing results of confirming an effect of changing an expression level of a BAX protein by a peptide having an amino acid sequence of SEQ ID NO: 1 and a peptide having an amino acid sequence of SEQ ID NO: 2, respectively.
Figure 10:
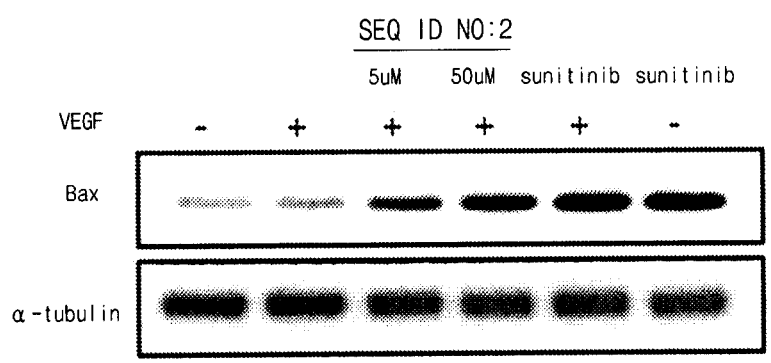
Figure 11:
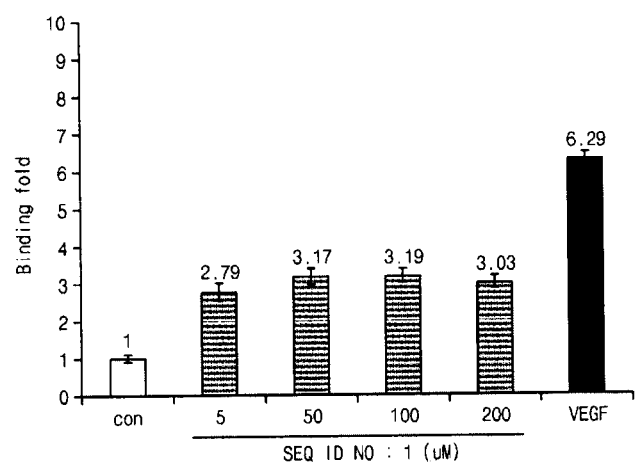
FIGS. 11 and 12 are graphs showing results of confirming whether a peptide having an amino acid sequence of SEQ ID NO: 1 and a peptide having an amino acid sequence of SEQ ID NO: 2 bind to VEGF receptors, respectively.
Figure 12:
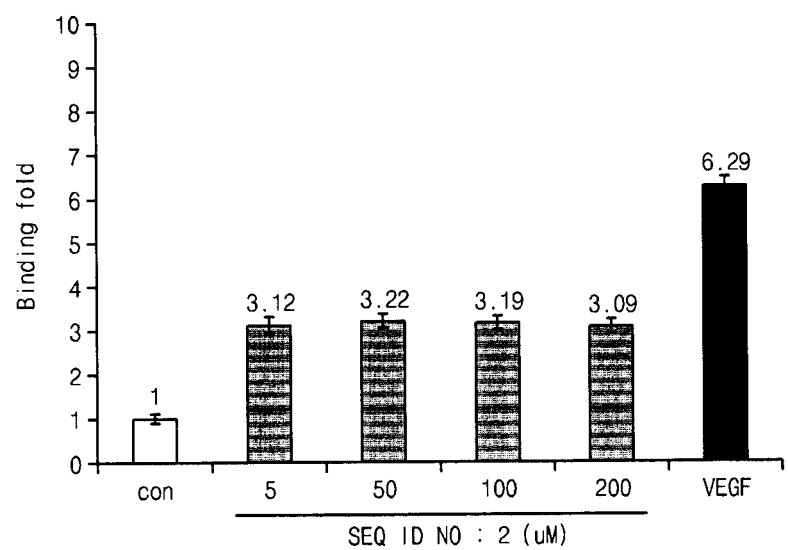

In addition, in order to confirm the effects of the peptides of the present invention on pro-apoptotic proteins of which expression is reduced by the VEGF, in a specific exemplary embodiment of the present invention, as a result of confirming the change in expression level of the BAX protein according to the treatment of the peptide having the amino acid sequence of SEQ ID NO: 1 or SEQ ID NO: 2 to the vascular endothelial cells, it was confirmed that the expression of the BAX protein, which was a protein inducing apoptosis, was reduced by the VEGF, while the expression of the BAX protein was increased concentration-dependently in a group treated with the peptides of the present invention (see FIGS. 9 and 10).

Figure 13:
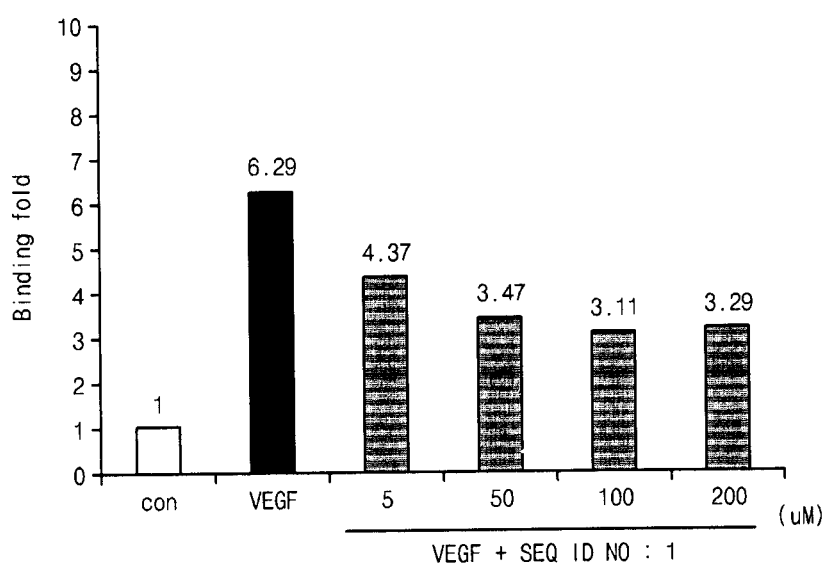
FIGS. 13 and 14 are graphs showing results of confirming whether a peptide having an amino acid sequence of SEQ ID NO: 1 and a peptide having an amino acid sequence of SEQ ID NO: 2 bind to VEGF receptors in competition with VEGFs, respectively.
Figure 14:
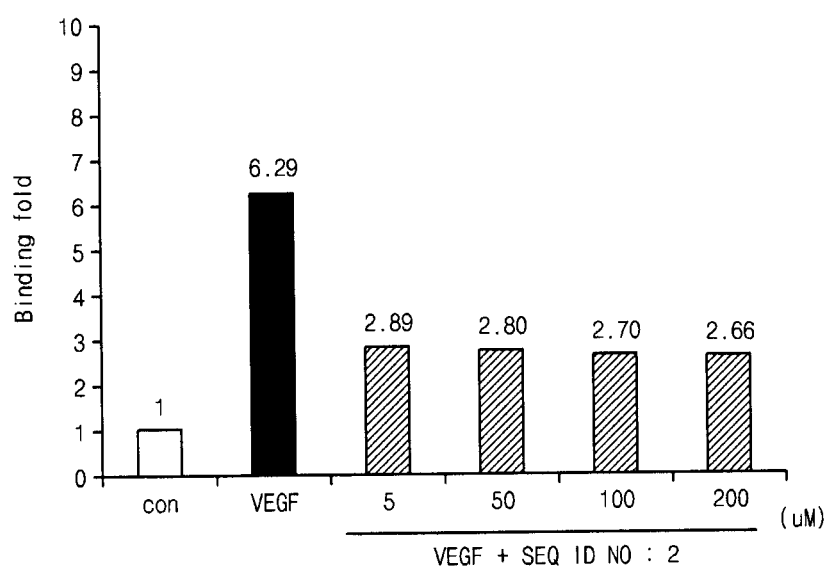

In addition, in order to confirm the competitive binding to the VEGF receptors of the peptides of the present invention, in a specific exemplary embodiment of the present invention, as a result of confirming whether the peptide having the amino acid sequence of SEQ ID NO: 1 or SEQ ID NO: 2 binds to the VEGF receptor, and whether the peptide binds to the VEGF receptor in competition with the VEGF, it was confirmed that the peptides of the present invention bind to a VEGFR2 competitively with the VEGF (see FIGS. 13 and 14).

Therefore, since the peptides of the present invention bind to the VEGF receptors in competition with the VEGFs and significantly inhibit the proliferation, migration and differentiation of vascular endothelial cells, it is obvious that the peptides have an activity that effectively inhibits angiogenesis, and thus, the peptides of the present invention may be effectively usable as an active ingredient of a composition for inhibiting excessive angiogenesis.

2. Pharmaceutical Compositions for the Treatment or Prevention of Angiogenesis-Related Diseases Another aspect of the present invention provides a pharmaceutical composition for the prevention or treatment of angiogenesis-related diseases containing a peptide having an amino acid sequence of SEQ ID NO: 1 or SEQ ID NO: 2 as an active ingredient.

The peptide containing the amino acid sequence of SEQ ID NO: 1 or SEQ ID NO: 2 is the same as the peptide described in the section of '1. peptide for inhibiting angiogenesis', and the detailed description cites the section of '1. peptide for inhibiting angiogenesis'. Hereinafter, only a unique configuration of the pharmaceutical composition for the treatment of the angiogenesis-related diseases will be described.

The angiogenesis-related disease refers to a disease caused by abnormally advancing angiogenesis, and includes cancer, diabetic retinopathy, prematurity retinopathy, neovascular glaucoma, melanoma, proliferative retinopathy, wet macular degeneration, psoriasis, hemophiliac joints, capillary hyperplasia in atherosclerotic plaques, keloids, wound granulation, vascular adhesion, rheumatoid arthritis, osteoarthritis, autoimmune diseases, Crohn's disease, restenosis, atherosclerosis, cat scratch disease, ulcers, glomerulonephritis, diabetic nephropathy, malignant neurosis, thrombotic microangiopathy, or renal glomerulopathy.

Therefore, since the diseases caused by angiogenesis may be prevented or treated by inhibiting angiogenesis, the composition comprising the peptides of the present invention as an active ingredient, which bind to the VEGF receptors in competition with the VEGFs and significantly inhibit the proliferation, migration and differentiation of vascular endothelial cells, may be effectively used for the treatment of angiogenesis-related diseases.

On the other hand, the peptides of the present invention may be carried in pharmaceutically acceptable carriers, such as colloidal suspensions, powders, saline, lipids, liposomes, microspheres, or nano spherical particles. These peptides may form or be related to a complex with a vehicle and may be carried in vivo by using carrying systems known in the art, such as lipids, liposomes, microparticles, gold, nanoparticles, polymers, condensation reagents, polysaccharides, polyamino acids, dendrimers, saponin, adsorption enhancing substances or fatty acids.

Besides, the pharmaceutically acceptable carrier may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil, which are generally used in preparation, but is not limited thereto. Further, the pharmaceutical composition may further include a lubricant, a wetting agent, a sweetening agent, a flavoring agent, an emulsifying agent, a suspending agent, a preservative, and the like in addition to the above ingredients.

The pharmaceutical composition of the present invention may be administered orally or parenterally (e.g., applied intramuscularly, intravenously, intraperitoneally, subcutaneously, intradermally, or topically) according to a desired method, and a dosage varies depending on the condition and weight of a patient, a degree of disease, a drug form, and route and time of administration, but may be appropriately selected by those skilled in the art.

The pharmaceutical composition of the present invention is administered in a pharmaceutically effective dose. In the present invention, the 'pharmaceutically effective dose' refers to a sufficient amount to treat the diseases at a reasonable benefit/risk ratio applicable to medical treatment, and an effective dose level may be determined according to factors including the type and severity of disease of a patient, activity of a drug, sensitivity to a drug, a time of administration, a route of administration, an emission rate, duration of treatment, and simultaneously used drugs, and other factors well-known in the medical field. The pharmaceutical composition according to the present invention may be administered as a separate therapeutic agent or in combination with other angiogenesis inhibitors, and may be administered simultaneously, separately, or sequentially with conventional therapeutic agents, and may be administered singly or multiply. It is important to administer an amount capable of obtaining a maximum effect with a minimal amount without side-effects by considering all the factors and this may be easily determined by those skilled in the art.

Specifically, the effective dose of the pharmaceutical composition of the present invention may vary depending on the age, sex, condition, and weight of a patient, absorbance of an active ingredient in vivo, an inactivation rate, an excretion rate, a disease type, and drugs to be used in combination, and may be increased or decreased according to a route of administration, the severity of obesity, sex, weight, age, and the like. For example, the peptide of the present invention may be administered at about 0.0001 μg to 500 mg, preferably 0.01 μg to 100 mg per kg of patient's body weight per day.

3. Health Functional Food for Improving Angiogenesis-Related Diseases

Yet another aspect of the present invention provides a health function food for the prevention or improvement of angiogenesis-related diseases containing a peptide having an amino acid sequence of SEQ ID NO: 1 or SEQ ID NO: 2 as an active ingredient.

The peptide containing the amino acid sequence of SEQ ID NO: 1 or SEQ ID NO: 2 is the same as the peptide described in the section of '1. peptide for inhibiting angiogenesis', and the detailed description cites the section of '1. peptide for inhibiting angiogenesis'. Hereinafter, only a unique configuration of the health functional food will be described.

Like the pharmaceutical composition, since the diseases caused by angiogenesis may be prevented or treated by inhibiting angiogenesis, the health functional food containing the peptides of the present invention as an active ingredient, which bind to the VEGF receptors in competition with the VEGFs and significantly inhibit the proliferation, migration and differentiation of vascular endothelial cells, may be effectively used for the prevention or improvement of angiogenesis-related diseases.

The health functional food may be used simultaneously or separately with a drug for treatment before or after the onset of the corresponding disease in order to prevent or improve the disease.

In the health functional food of the present invention, the active ingredient may be added to the food as it is or used with other foods or food ingredients, and may be appropriately used according to a general method. The mixing amount of the active ingredients may be suitably determined according to the purpose of use thereof (for prevention or improvement). In general, in preparation of foods or beverages, the composition of the present invention may be added in an amount of preferably 15 wt % or less, more preferably 10 wt % or less with respect to raw materials. However, in the case of long-term ingestion for the purpose of health and hygiene or health regulation, the amount may be equal to or lower than the above range.

The health functional food of the present invention may contain other ingredients as required ingredients without particular limitation, in addition to the active ingredient. For example, like general beverages, various flavoring agents or natural carbohydrates may be contained as an additional ingredient. Examples of the above-mentioned natural carbohydrates may include conventional sugars, such as monosaccharides such as glucose, fructose and the like; disaccharides such as maltose, sucrose and the like; and polysaccharides such as dextrin, cyclodextrin and the like, and sugar alcohols such as xylitol, sorbitol, erythritol, and the like. As flavoring agents other than those described above, natural flavoring agents (tauumatin, stevia extract (e.g., Rebaudioside A, glycyrginine, etc.)) and synthetic flavoring agents (saccharin, aspartame, etc.) may be advantageously used. The ratio of the natural carbohydrates may be appropriately determined by the selection of those skilled in the art.

In addition, the health functional food of the present invention may contain various nutrients, vitamins, minerals (electrolytes), flavoring agents such as synthetic and natural flavoring agents, coloring agents, and enhancers (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, and the like. These ingredients may be used independently or in combination, and the ratio of these additives may also be appropriately selected by those skilled in the art.

Hereinafter, the present invention will be described in detail by Examples and Experimental Examples.

However, the following Examples and Experimental Examples are just illustrative of the present invention, and the contents of the present invention are not limited to the following Examples and Experimental Examples.

[Preparation Example 1] Preparation of Peptides

A peptide having an amino acid sequence of SEQ ID NO: 1 and a peptide having an amino acid sequence of SEQ ID NO: 2 shown in Table below were synthesized using an automated peptide synthesizer (Milligen 9050, Millipore, USA), respectively, and these synthesized peptides were purified using C18 reversed-phase high performance liquid chromatography (HPLC) (Waters Associates, USA), respectively. The column used ACQUITY UPLC BEH300 C18 (2.1 mm×100 mm, 1.7 µm, Waters Co, USA).

TABLE 1

| SEQ ID NO. | Peptide sequence |
|---|---|
| 1 | NKNFGYDLYR |
| 2 | IHGTYKELL |

[Experimental Example 1] Confirmation of Effect of Inhibiting Proliferation of Vascular Endothelial Cells In order to confirm an effect of inhibiting the proliferation of vascular endothelial cells, the peptides prepared in Preparation Example 1 were treated to vascular endothelial cells, respectively, and then MTT analysis was performed.

Specifically, human umbilical vein endothelial cells (HUVEC) were inoculated in a 96-well plate at a density of $4 \times 10^3$ cells/well and then incubated overnight. Thereafter, after the medium was changed to a medium added with 1% serum, a VEGF (20 ng/ml) and the peptide of the present invention were treated for each concentration, respectively, and incubated for 3 days. However, 2 µm of sunitinib was used as a positive control group.

In addition, in order to confirm the effect of inhibiting the proliferation, 4 mg/ml of a thiozolyl blue tetrazolium bromide (MTT) solution was added to each well, formazan generated after reaction for 4 hours was dissolved by DMSO treatment, and then the absorbance was measured at a wavelength of 560 nm using a microplate reader. However, the measured absorbance values were shown by calculating relative rates based on an untreated control group.

Figure 2:
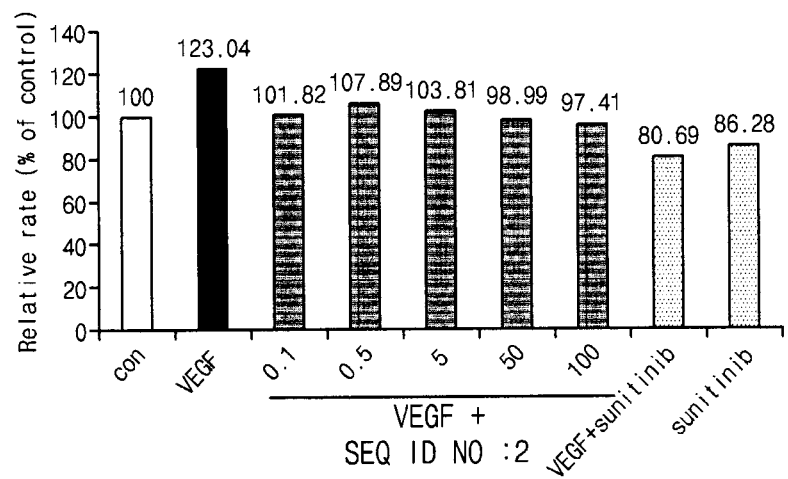

As shown in FIGS. 1 and 2, the peptides of the present invention significantly inhibited the proliferation of vascular endothelial cells increased by the VEGF.

For angiogenesis, since vascular endothelial cells are proliferated and then blood vessels are formed through invasive growth and differentiation, from the above results, it can be seen that the peptides of the present invention significantly inhibit angiogenesis by inhibiting the proliferation of vascular endothelial cells.

[Experimental Example 2] Confirmation of Effect of Inhibiting Differentiation of Vascular Endothelial Cells In order to confirm the effect of inhibiting the differentiation of vascular endothelial cells, the two peptides prepared in Preparation Example 1 were treated to the vascular endothelial cells, respectively, and then a tube formation assay was performed.

Specifically, HUVEC cells were inoculated in a 96-well plate at a density of 1.5×10³ cells/well and incubated overnight, and then the medium was replaced with serum-free media, and then a VEGF (20 ng/ml) and the peptide of the present invention were treated by concentration and incubated for 1 day. However, 2 μm of sunitinib was used as a positive control group. After the incubation was completed, the measurement of tube formation was visually observed using an optical microscope, and the number of nodules was measured together.

Figure 3A:
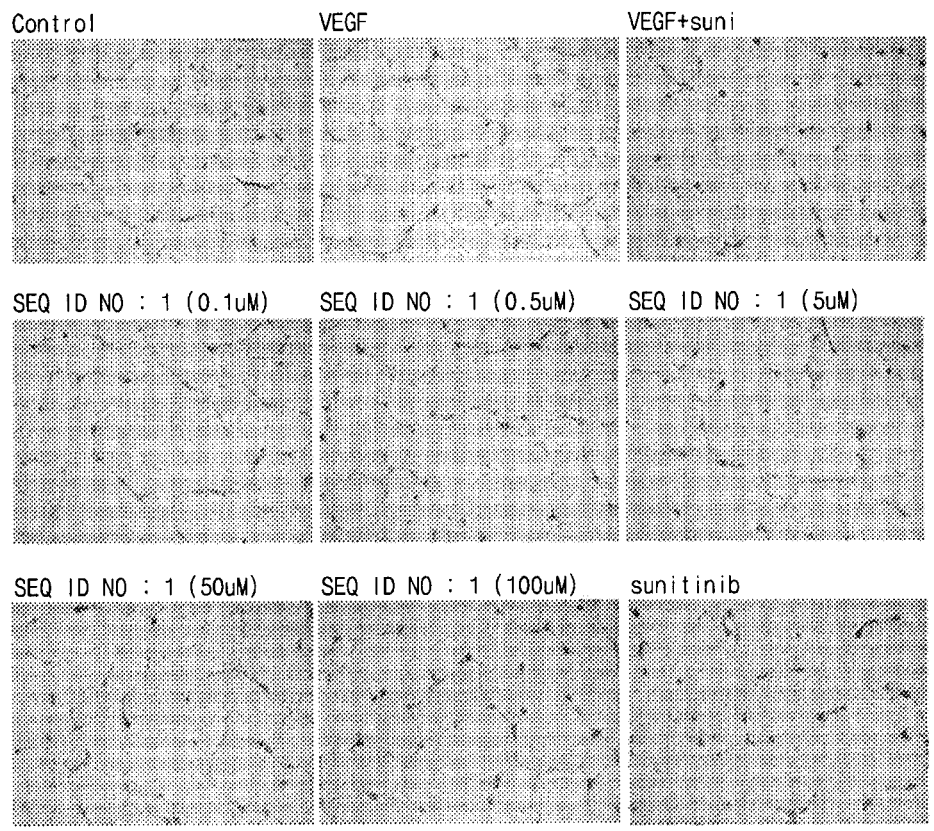
FIGS. 3(a), 3(b), 4(a), and 4(b) are diagrams and graphs showing results of confirming an effect of inhibiting the differentiation of vascular endothelial cells by a peptide having an amino acid sequence of SEQ ID NO: 1 and a peptide having an amino acid sequence of SEQ ID NO: 2, respectively.
Figure 3B:
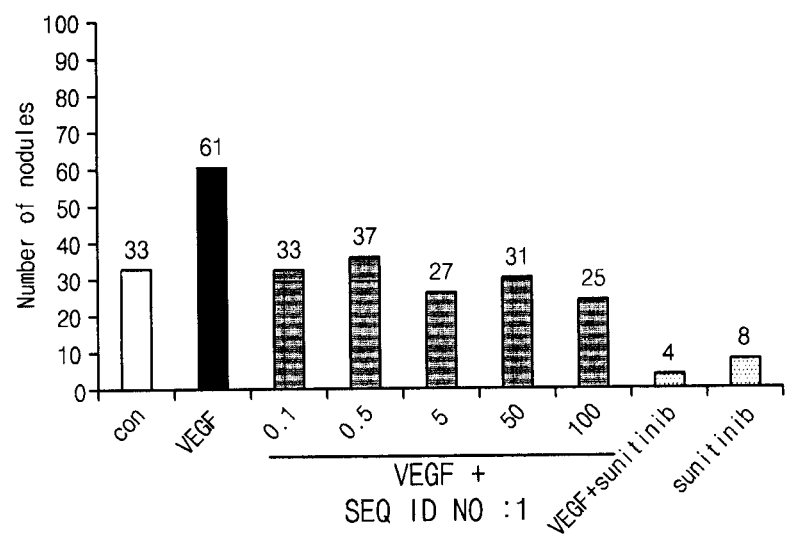
Figure 4A:
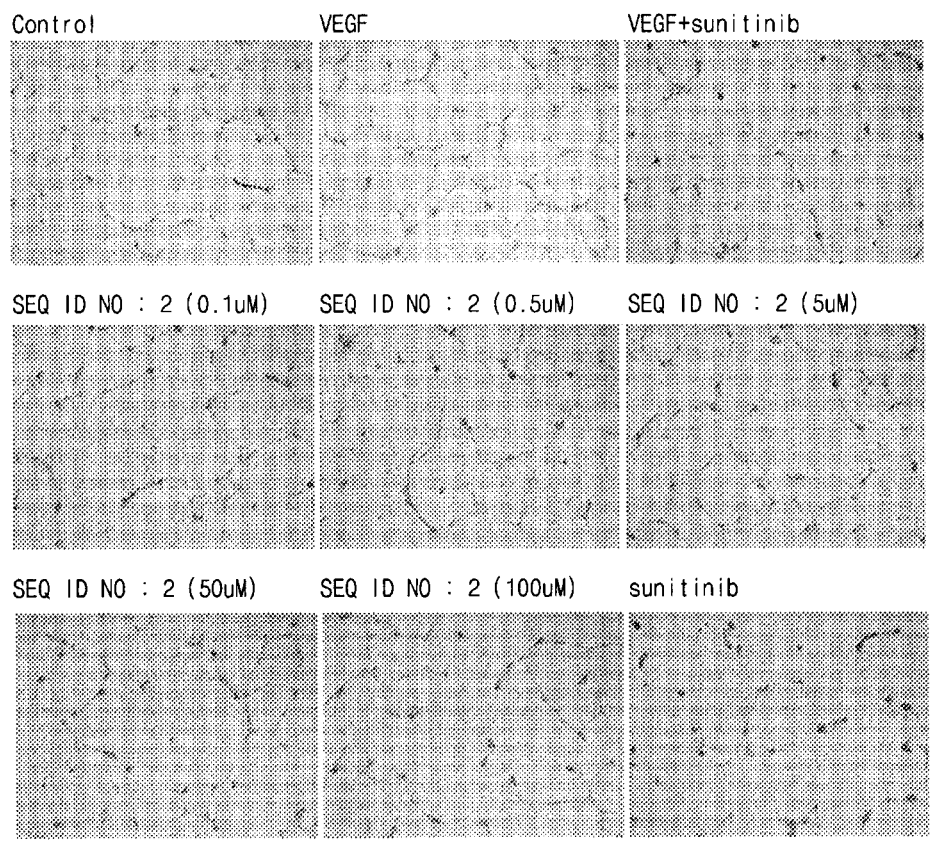
Figure 4B:
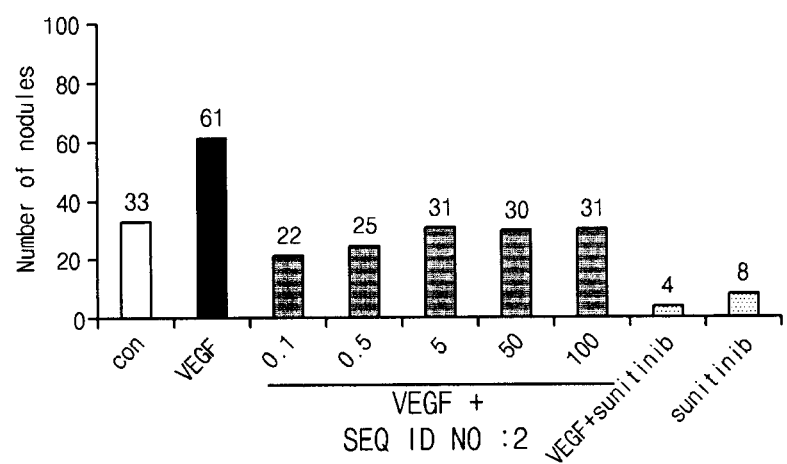

As shown in FIGS. 3 and 4, it was confirmed that the VEGF significantly increases the tube formation and the number of nodules of vascular endothelial cells, but the peptides of the present invention inhibit the tube formation of the vascular endothelial cells and significantly reduce the number of nodules.

INDUSTRIAL AVAILABILITY

A peptide for inhibiting angiogenesis consisting of an amino acid sequence represented by SEQ ID NO: 1 or 2 of the present invention and a composition containing the same as an active ingredient may exhibit an excellent effect of prevention or treatment on diseases caused by excessive angiogenesis to be very effectively used industrially.

[Sequence Listing Freetext]

```
SEQ ID NO: 1:
Asn Lys Asn Phe Gly Tyr Asp Leu Tyr Arg

SEQ ID NO: 2:
Ile His Gly Thr Tyr Lys Glu Leu Leu
```

The invention claimed is:

1. A synthetic peptide for inhibiting angiogenesis consisting of an amino acid sequence of SEQ ID NO: 1 or SEQ ID NO: 2 wherein the peptide binds to a vascular endothelial growth factor (VEGF) receptor.

2. The peptide for inhibiting the angiogenesis of claim 1, wherein an N- or C-terminus of the peptide is bound to a protective group selected from the group consisting of an acetyl group, a fluorenylmethoxy carbonyl group, a formyl group, a palmitoyl group, a myristyl group, a stearyl group, and polyethylene glycol (PEG).

3. The peptide for inhibiting the angiogenesis of claim 1, wherein the peptide inhibits the proliferation, differentiation, and migration of vascular endothelial cells.

4. The peptide for inhibiting the angiogenesis of claim 1, wherein the VEGF receptor is a vascular endothelial growth factor receptor 2 (VEGFER2).

5. The peptide for inhibiting the angiogenesis of claim 1, wherein the peptide binds to a VEGF receptor in competition with a VEGF.

6. A method of inhibiting angiogenesis in a subject comprising administering a therapeutically effective amount of the peptide of claim 1 to the subject in need thereof.

7. The method of claim 6, wherein the peptide inhibits the proliferation, differentiation, and migration of vascular endothelial cells.

* * * * *

---

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Peptide 1

<400> SEQUENCE: 1

Asn Lys Asn Phe Gly Tyr Asp Leu Tyr Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Peptide 2

<400> SEQUENCE: 2

Ile His Gly Thr Tyr Lys Glu Leu Leu
1               5
```